United States Patent [19]

Stokes et al.

[11] Patent Number: 4,787,895
[45] Date of Patent: Nov. 29, 1988

[54] ADHESIVELY HELD SPIRAL WOUND TAMPON AND METHOD OF ITS FORMATION

[75] Inventors: Bruce G. Stokes, Cherokee County, Ga.; Richard R. Tews; Donald A. Sheldon, both of Outagamie County, Wis.

[73] Assignee: Kimberly-Clark Corporation, Neenah, Wis.

[21] Appl. No.: 55,680

[22] Filed: May 29, 1987

[51] Int. Cl.$^4$ .............................................. A61F 13/16
[52] U.S. Cl. ................................... 604/358; 604/904
[58] Field of Search ............... 604/358, 904, 378, 379, 604/385

[56] References Cited

U.S. PATENT DOCUMENTS 4,217,900  8/1980  Wiegner et al. .................... 604/904

Primary Examiner—Stephen C. Pellegrino
Attorney, Agent, or Firm—Paul A. Leipold; Thomas J. Connelly

[57] ABSTRACT

The invention is generally accomplished by providing a generally rectangular blank of absorbent material. Adjacent one strip of the rectangular sheet is placed a generally continuous line of adhesive. The rectangular blank is then wound and compressed to form a tampon. As the tampon is compressed the adhesive fuses one end of the wound tampon. The blank is provided with a string prior to winding that is also adhesively connected to the tampon. As the tampon expands in the vagina it will open at the insertion end but not expand significantly at the withdrawal end. Therefore this tampon is easier to withdraw but expands readily at the insertion end to prevent leakage. The tampon also resists telescoping during withdrawal.

15 Claims, 5 Drawing Sheets

FIG. 5

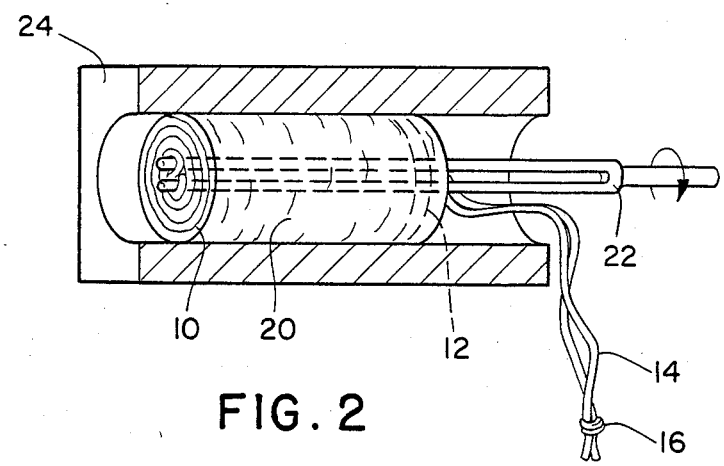
FIG. 2
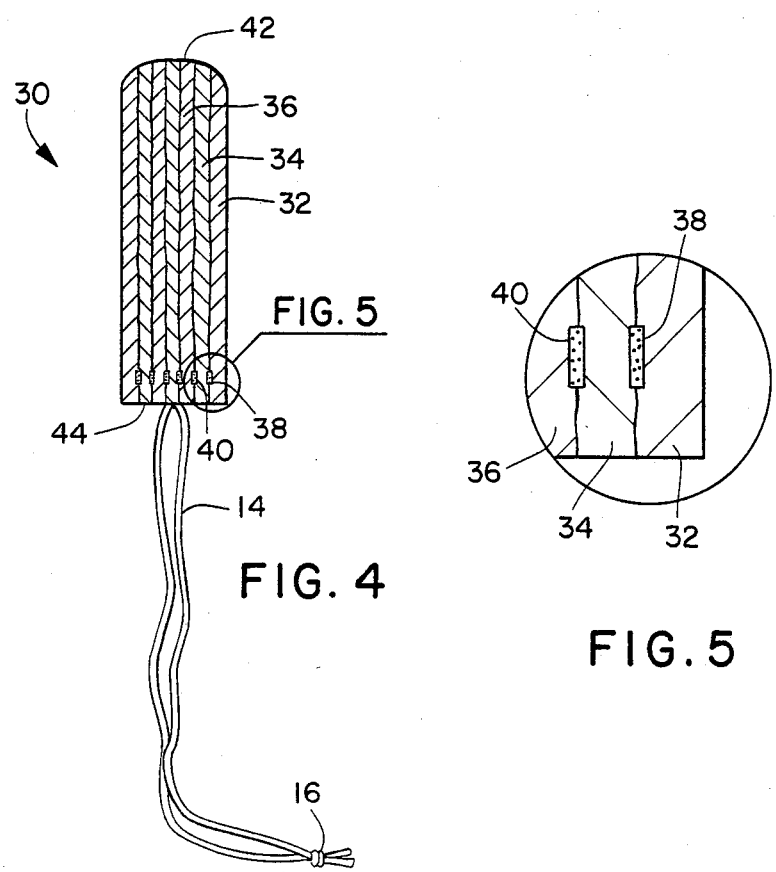
FIG. 4
FIG. 5

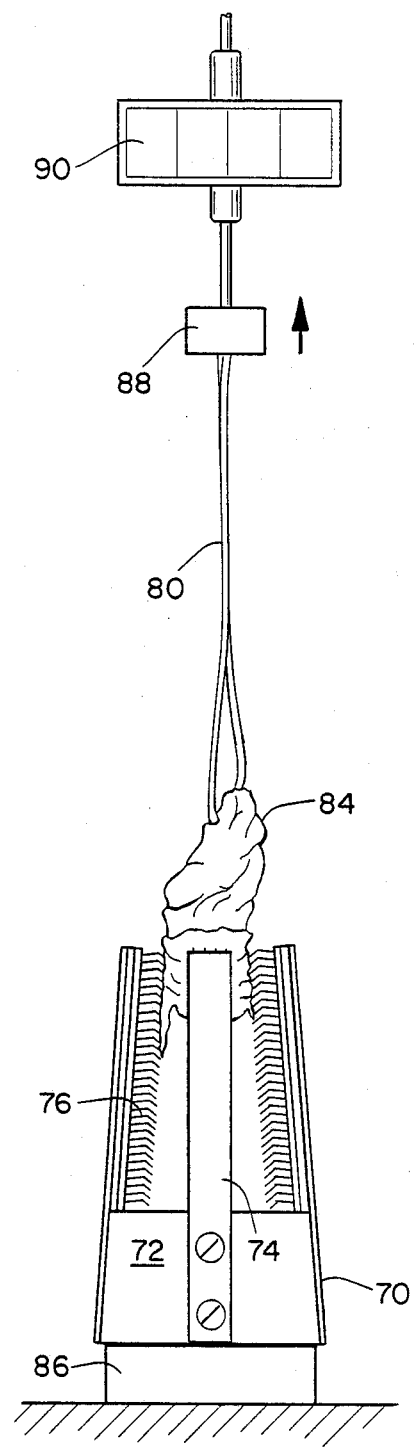
FIG. II

ADHESIVELY HELD SPIRAL WOUND TAMPON AND METHOD OF ITS FORMATION

TECHNICAL FIELD

This invention relates to a tampon and particularly a tampon having a wound pledget.

BACKGROUND ART

Recently tampons having wound pledgets have become increasingly popular, particularly in Europe. These tampons are formed from a flat absorbent web which is rolled in a jelly roll type of configuration and compressibly set with or without the presence of heat. Examples of machines currently used for the manufacture of such tampons employ a shaping receptacle which fits around the tampon pledget as the pledget is wound. The machines, however, differ in the means for winding the tampon. One of these machines is made by Karl Ruggli AG, Fisibach, Switzerland. The Ruggli machine employs a two-pronged fork which engages one end of the web. The fork is rotated while the outside of the web is in contact with the shaping receptable to form a rolled cylindrical pledget. The other machine known as the Fulu and made by K. Fassbind-Ludwig & Co., Fulu Maschinenbau, Wugen, Switzerland utilizes a vacuum mandrel for holding one end of the web. As is the case with the Ruggli machine the web is rotated while a portion of the web which is to be the outer surface is in contact with the configuration-forming receptable.

Both of these machines have the advantage of rapidly forming a tampon from a web of absorbent material, the web being easily produced on conventional machinery. The tampon produced from both machines, however, suffers from the same disadvantage. After the tampon is used and withdrawal is desired the pledget tends to unwind. This unwinding, due to the exertion of withdrawal force on the string, produces an elongated twisted unsightly tampon which is messy to handle and difficult to withdraw. Attempts at minimizing the telescoping problem have included utilizing adhesive in localized areas so that during the winding and compressive setting of the tampon the adhesive will be activated. This step is complicated, and also could interfere with tampon absorbency.

It is also known that integrity of conventional absorbent cellulosic material which is used in a tampon of this construction, typically, can be increased by local compression, i.e. by embossing or contacting with needles. While this step has been attempted on the wound tampons during the winding process per se, its success has been limited.

In U.S. Pat. No. 4,373,529—Lilaonitkul, et al. it has been proposed that the telescoping of wound tampons be minimized by the formation of the tampon in a truncated cone shape.

In U.S. Pat. No. 2,330,257—Bailey it has been proposed in FIG. 21 of that patent to size the lower portion of the tampon with a liner such as glue in order to prevent expansion of the lower end when wet.

In U.S. Pat. No. 4,335,721—Mathews it has been proposed that a tampon be formed from parallel fusible fibers that may be joined using a fusing string that traverses the fibers.

However, there remains a need for a low-cost, reliable method of forming a non-telescoping tampon utilizing the conventional fiber materials used in forming tampons.

DISCLOSURE OF THE INVENTION

An object of the invention is to overcome disadvantages of prior tampon products and processes of formation of tampons.

Another object is to provide a low-cost method of adhesively connecting wound tampons.

A further object of the invention is to provide a tampon that is easy to withdraw.

A further additional object of the invention is to provide a tampon that does not telescope when removed after use.

These and other objects of the invention are generally accomplished by providing a generally rectangular blank of absorbent material. Adjacent one edge of the rectangular sheet is placed a generally continuous line of adhesive. The rectangular blank is then wound and compressed to form a tampon. As the tampon is compressed the adhesive fuses one end of the wound tampon. The blank is provided with a withdrawal cord prior to winding that is also adhesively connected to the tampon. As the tampon expands in the vagina it will open at the insertion end but not expand significantly at the withdrawal end. Therefore this tampon is easier to withdraw but expands readily at the insertion end to prevent leakage. The tampon as it is adhesively connected will not telescope as the tampon is withdrawn.

BRIEF DESCRIPTION OF THE DRAWINGS

FIG. 2 is a view of a tampon preform prior to compression.

FIG. 4 is a cross-sectional view of the tampon of the invention on line 4—4 of FIG. 3.

FIG. 5 is an enlarged view of section 5 of FIG. 4.

FIGS. 9, 10 and 11 are views of a device for utilization in the testing of tampon resistance to telescoping.

MODES OF PRACTICE IN THE INVENTION

This invention has numerous advantages over the prior art. The prior methods of bonding rolled tampons either did not prevent telescoping or resulted in a tampon that was compressed to such degree that it would not readily absorb menstrual fluid or reexpand to occlude the vaginal cavity. Further the tampon of the instant invention has the advantage that it expands such that the forward or insertion end opens while the rearward portion does not significantly expand. Therefore, the tampon is easier to withdraw from the vagina after use. Further the adhesive connection of the layers provides positive bonding of the layers to prevent telescoping without any reduction in expansion that would be associated with high compression to achieve binding. These and other advantages will become apparent from the drawings and detailed description below.

Figure 1:
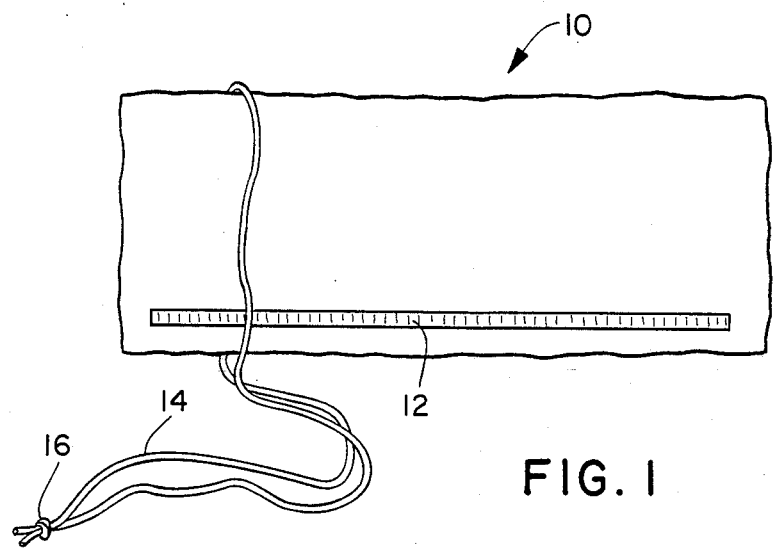
FIG. 1 is a view of the fibrous blank used in formation of the tampon of the invention.

Illustrated in FIG. 1 is a blank 10 that is rolled to form the tampon of the invention. The blank is generally a fibrous material of cellulose fibers, cotton, rayon, or mixtures thereof. These fibers further may be impregnated with a superabsorbent material. Preform 10 further is provided with an adhesive 12 that has been applied adjacent to one of the longer borders of the rectangular fibrous preform 10. The preform further has a withdrawal cord 14 that is looped around the preform 10 and joined at knot 16.

Figure 3:
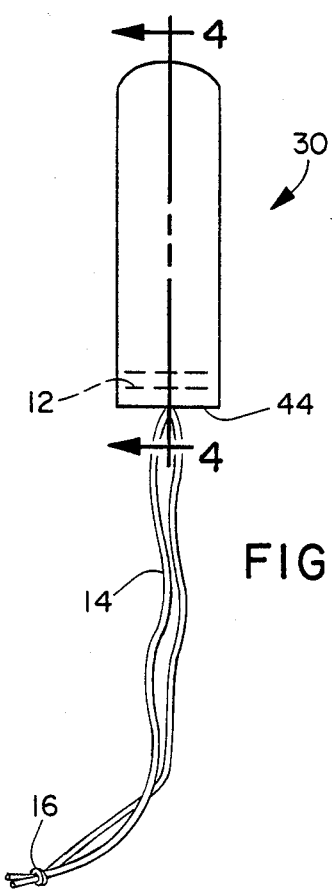
FIG. 3 is a tampon of the invention.

FIG. 2 illustrates a tampon preform 20 that is wound from the fibrous preform 10. The tampon preform 20 is shown as wound by rotation of fork means 22. The tampon preform 20 is in a portion of forming die 24. The forming die will apply heat and compression to compress the tampon preform 20 into a tampon 30 as illustrated in FIG. 3. Tampon 30 has the adhesive 12 wound on the inner surface and acting to join the wound bottom portion of the tampon.

As illustrated in FIG. 4 and FIG. 5 the compressed tampon is made of a series of layers such as 32, 34, and 36. Between each layer and adjoining adjacent layers are the adhesives such as adhesive 38 joining layers 32 and 34 and adhesive 40 joining layers 34 and 36. Further the adhesive 12 is in contact with the withdrawal cord 14 and provides an adhesive connection to aid in binding of the withdrawal cord 14 to the tampon 30.

Figure 6:
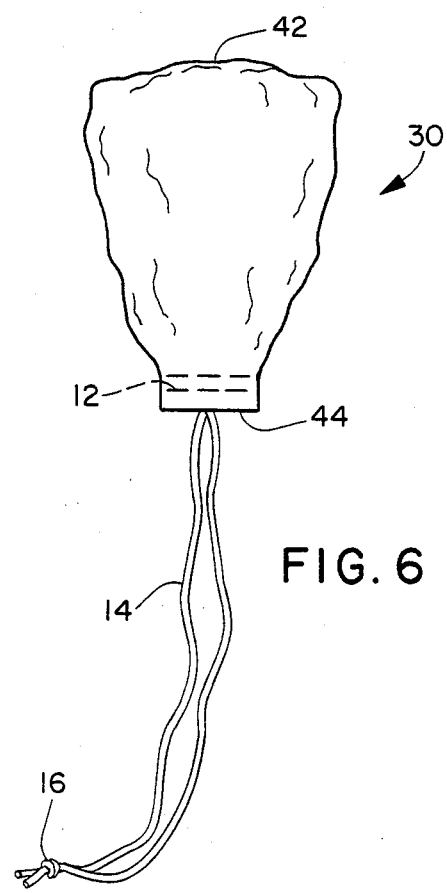
FIG. 6 is a view of a tampon of the invention as expanded after use.

Illustrated in FIG. 6 is the tampon after use. The tampon has expanded greatly at the insertion end 42, but has undergone much less expansion at the withdrawal end 44 where the cord 14 is connected. New adhesive 12 has restricted expansion of the withdrawal end 44 thereby allowing easier withdrawal of the compressed tampon. Further the relatively large expansion of end 42 helps to prevent leaking of the tampon during use.

Figure 7:
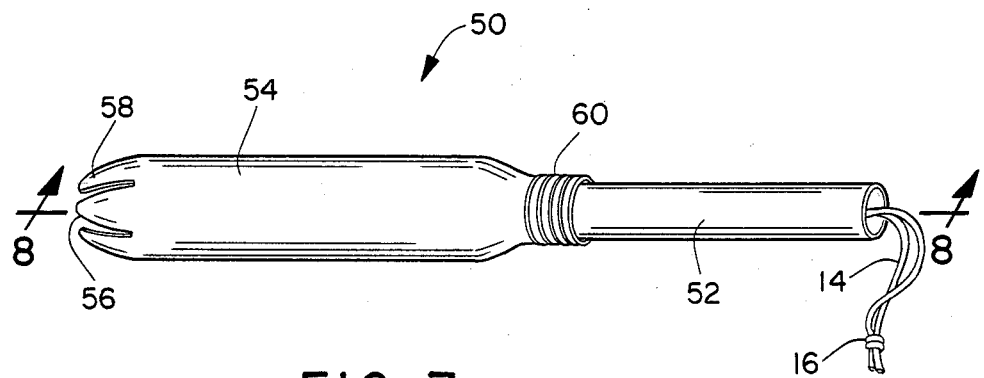
FIG. 7 is a perspective view of a tampon applicator suitable for use with the tampon of the invention.
Figure 8:
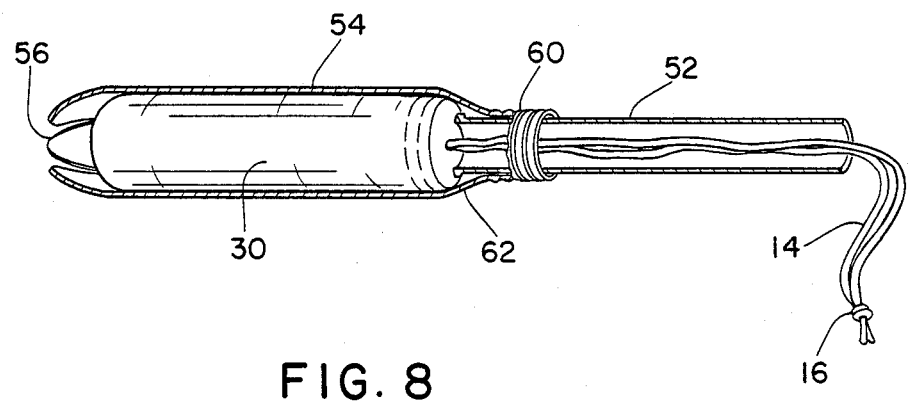
FIG. 8 is a cross-sectional view of the tampon applicator of FIG. 7 on line 8—8 of FIG. 7.

FIGS. 7 and 8 illustrate the tampon of the invention with a two-piece applicator prior to use. The applicator 50 has an inner tube 52 and an outer tube 54. The insertion end 56 is provided with a series of petals 58 that open as the inner tube 52 is pressed forward into outer tube 54 and eject the tampon 30 through the petals 58 at the insertion end 56. The outer tube is provided with a gripping portion 60. The inner tube is provided with an expanded portion 62 at the insertion end to prevent withdrawal of the inner tube 52 from the outer tube 54.

The absorbent utilized in the invention may be any suitable material. Generally tampons may be made from any fiber material that is absorbent and safe for such use. Typical of such materials are cellulose fibers, rayon, cotton fibers and mixtures of these fibers. Further it is possible that superabsorbent particles may be embedded in the fibers or superabsorbent fibers such as the Aqualon ® fibers of Hercules Company that are a combination of cellulose polymer may be utilized. Further the absorbent may be microcreped such as the material disclosed in U.S. Pat. No. 4,627,849—Walton to provide additional absorption.

The string on the tampon of the invention may be formed of any suitable material that is non-wicking and safe. Typical of such materials are cotton, rayon, polyester, polypropylene, and blends thereof. A preferred material is polyester as it is non-wicking and low in cost.

The adhesive utilized in the invention may be any suitable material that is safe for use in tampons, does not dissolve or weaken in menstrual fluid and provides sufficient adhesion to maintain the tampon to prevent telescoping. Adhesive materials include polyester films and hot melt adhesives applied in a hot flowable state and powders such as polypropylene. A preferred material is a fibrous sheet or a film of polyethylene or polypropylene as it is low in cost, effective and safe as no residual polymers are available to wick from the material. Preferred hot melt adhesives are the ethylene-vinyl acetate (EVA) resins as many of these are generally safe for hygienic uses such as tampons.

While illustrated in FIGS. 7 and 8 with a two-piece tampon applicator the tampons of the invention may also be utilized in other application methods such as in stick tampons or in digitally inserted tampons.

EXAMPLES

The following examples are intended to be illustrative of the invention. Parts are by weight unless otherwise set forth.

EXAMPLE 1

A fibrous blank for formation of a tampon having a width of about 2 inches and a length of about 9 inches and a weight of about 3 grams is prepared from a 95% rayon mixture. A strip of hot melt adhesive (Primacor 5991 of a composition of ethylene acrylic acid) is laid down in a bead about ¼ inch from one long edge of the tampon blank. The blank has a withdrawal string of polyester looped around the blank from one end. The blank is then wound to form a tampon preform. The hot melt is placed in a bead along substantially the entire edge and has a weight of about 0.3 grams. The tampon preform is compressed in a mold that is maintained at about 125° C. to form a tampon. The compressed tampon is about two inches long and about one-half inch in diameter. The end toward which the string is located is first wound so as to form the inside of the tampon.

Figure 9:
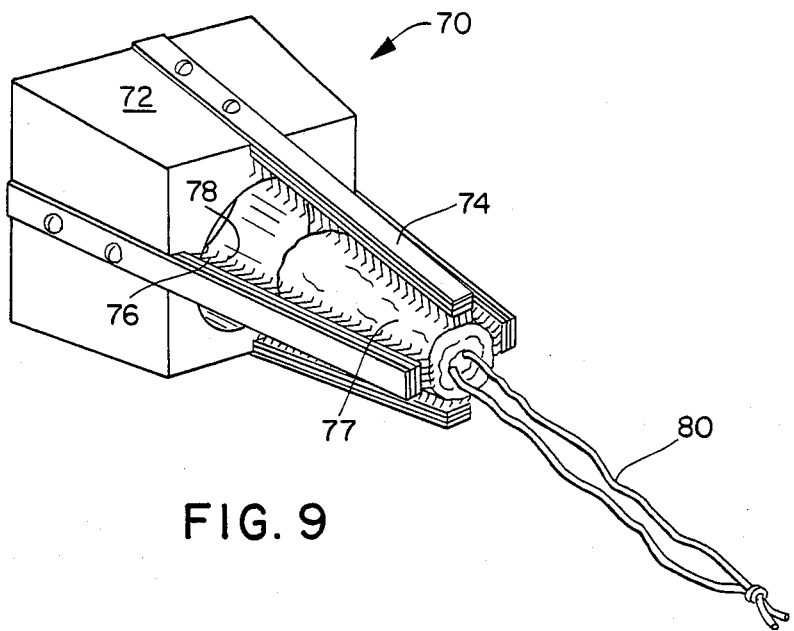
Figure 10:
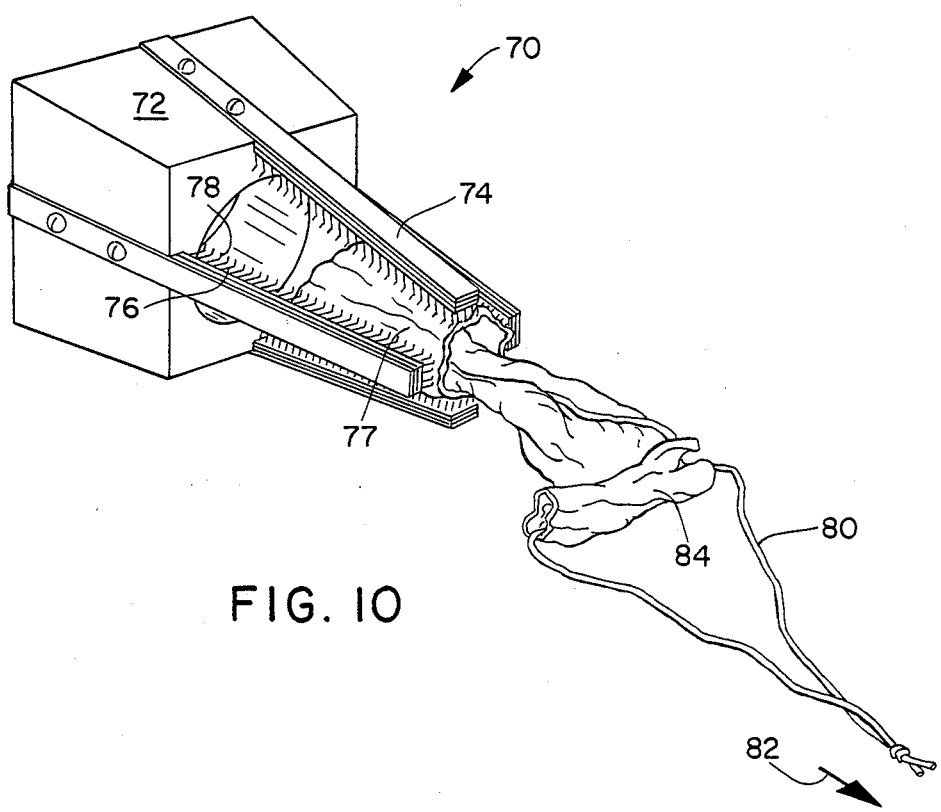

The tampon is tested in a device as illustrated in FIGS. 9, 10, and 11. As illustrated in FIGS. 9 and 10 the device 70 comprises a solid base member 72 that is provided with four upstanding support members 74. Each of the support members is provided with a series of pins 76 having points that face toward the base 72. A tampon 77 is wet with about 8 grams of water and then placed into device 70 between the four upstanding portions 74. This insertion is with the direction of the pinpoints 78. Insertion from the opening in base 72 would be against the direction of the pinpoints 78. After the tampon 77 is inserted, generally flush with the end of upstanding pin-carrying members 74, the withdrawal cord 80 is pulled in the direction of arrow 82 until the tampon telescopes with the center portion 84 pulling free from the outer portion as shown in FIG. 10. Measurement of this force required to telescope the tampon from the device allows comparison of various binding systems for the spiral wound tampons. As illustrated in FIG. 11 the device 70 is placed in a clamp 86 and the cord 80 is fastened in clamping means 88 and then drawn with upward force. The digital scale 90 provides the reading of the pressure required to telescope the center section 84 from the grip of pins 76 in the pinholders 74.

Tampons formed as in Example 1 are tested and found to have a telescoping force requirement of about 2500 grams to telescope.

EXAMPLE 2

A tampon is formed as in Example 1 except that a hot melt adhesive Primacor 5990 (a product of Dow Chemical Company believed to comprise ethylene acrylic acid resin) is utilized in a loading of 0.3 grams per tampon blank as the adhesive for the tampon. The telescoping force is measured and found to be about 2200 grams.

EXAMPLE 3

The method of Example 1 is repeated except that the adhesive is a Sharnet ™ bonding film of polyethylene meltblown material. A strip of about ½ inch width having a weight of about 0.3 grams is utilized. When tested, a telescoping force of about 2000 grams is indicated.

EXAMPLE 4

The method of Example 1 is repeated except that a hot melt glue from Bostick, identified as product No. 6370 having a composition of ethylene-vinyl acetate and polyethylene copolymer, is utilized at a loading of about 0.3 grams. This tampon when tested is found to have a telescoping force of about 1620 grams.

EXAMPLE 5

Control

The method of Example 1 is repeated except that a starch based water carried adhesive of Borden, Inc. is utilized in construction. The tampon is found to have a telescoping force of 1200 grams.

EXAMPLE 6

Control

The process of Example 1 is repeated except that no adhesive is added on the edge of the tampon preform. This tampon is found to have a telescoping force of about 1200 grams.

As can be seen from the above examples, the addition of adhesive to the tampon significantly improves its ability to resist telescoping. Further the examples show that the adhesive should not have a water base. Unless the adhesive is resistant to bond degradation by water, the performance is not improved. Tampons of the invention have a greater than 25 percent improvement in resistance to telescoping over unbound tampons. The tampons further have an increased resistance to leaking.

While the invention has been described with reference to specific embodiments and materials, it will be understood by those of ordinary skill in the art that there are other variations of the invention. For instance, the tampons of the invention could be used for other medical uses such as absorption of blood during operations or for absorption of liquids during dental treatment. Further the tampons could be provided with a cover material if this was desired. These and other embodiments are intended to be included by the invention that is only to be limited by the scope of the claims attached hereto.

We claim:

1. A method of forming a tampon comprising providing an elongate rectangular absorbent blank having long sides and shorter ends, placing an adhesive band onto said blank in at least a portion of the area parallel to one of the long sides of said rectangular blank, winding said blank to form a cylindrical tampon blank, compressing said blank to form a tampon adhesively held together adjacent one end wherein said adhesive is concealed on the inner surface of said wound blank and wherein said withdrawal cord exits said tampon adjacent the end of said tampon adhesively held together.

2. The method of claim 1 wherein said adhesive is heat curable web.

3. The method of claim 1 wherein said blank is wound so that said adhesive is located near one end of said cylindrical tampon blank.

4. The method of claim 1 wherein said absorbent blank is microcreped.

5. The method of claim 1 wherein said adhesive is placed as a continuous strip onto said blank.

6. The method of claim 1 wherein said withdrawal cord exits said tampon adjacent the end of said tampon adhesively held together.

7. The method of claim 1 wherein said adhesive comprises a hot melt adhesive.

8. The method of claim 7 wherein said adhesive comprises an ethylene vinyl acetate resin.

9. A tampon comprising an absorbent wound to form a cylinder, an adhesive band between layers of said absorbent, said adhesive band being located adjacent the withdrawal end of said tampon and a withdrawal cord exiting said tampon at said withdrawal end wherein said adhesive is located between the layers of the wound absorbent and thereby concealed in the wound tampon absorbent, and said tampon will not expand substantially at said withdrawal end.

10. The tampon of claim 9 wherein said absorbent comprises a microcreped sheet.

11. The tampon of claim 9 wherein said adhesive comprises polyethylene.

12. The tampon of claim 9 wherein said absorbent comprises at least one fibrous material selected from the group consisting essentially of cellulosic fibers, rayon, cotton and mixtures thereof.

13. The tampon of claim 9 wherein said tampon has a greater than 25 percent increase in resistance to telescoping compared to tampons not adhesively connected.

14. The tampon of claim 9 wherein said adhesive is water insoluble.

15. The tampon of claim 9 wherein said adhesive comprises a hot melt adhesive.

* * * * *

UNITED STATES PATENT AND TRADEMARK OFFICE
CERTIFICATE OF CORRECTION

PATENT NO. : 4,787,895
DATED : November 29, 1988
INVENTOR(S) : B. G. Stokes et al It is certified that error appears in the above-identified patent and that said Letters Patent is hereby corrected as shown below:

Column 5, Line 5, delete "1/2" and substitue therefor --1/4--.

Signed and Sealed this

Twenty-seventh Day of June, 1989

Attest:

DONALD J. QUIGG

*Attesting Officer*  *Commissioner of Patents and Trademarks*